(12) United States Patent
Lee

(10) Patent No.: US 10,471,117 B2
(45) Date of Patent: Nov. 12, 2019

(54) METHOD OF TREATMENT OF UREMIA ASSOCIATED WITH RENAL DYSFUNCTION LONG AFTER TRANSPLANT

(71) Applicant: Chen-Yu Lee, Taipei (TW)

(72) Inventor: Chen-Yu Lee, Taipei (TW)

( * ) Notice: Subject to any disclaimer, the term of this patent is extended or adjusted under 35 U.S.C. 154(b) by 205 days.

(21) Appl. No.: 15/855,252

(22) Filed: Dec. 27, 2017

(65) Prior Publication Data

US 2019/0192609 A1  Jun. 27, 2019

(51) Int. Cl.

| | | |
|---|---|---|
| A61K 36/00 | (2006.01) |
| A61K 36/9068 | (2006.01) |
| A61K 36/428 | (2006.01) |
| A61K 36/40 | (2006.01) |
| A61K 36/64 | (2006.01) |
| A61K 36/8945 | (2006.01) |
| A61K 36/232 | (2006.01) |
| A61K 36/46 | (2006.01) |
| A61K 36/39 | (2006.01) |
| A61K 36/815 | (2006.01) |
| A61K 36/54 | (2006.01) |
| A61K 36/714 | (2006.01) |
| A61K 36/076 | (2006.01) |
| A61K 36/756 | (2006.01) |
| A61K 36/21 | (2006.01) |
| A61K 36/284 | (2006.01) |
| A61K 36/258 | (2006.01) |
| A61K 35/32 | (2015.01) |
| A61K 33/06 | (2006.01) |
| A61K 36/708 | (2006.01) |
| A61P 13/12 | (2006.01) |

(52) U.S. Cl.
CPC .......... *A61K 36/9068* (2013.01); *A61K 33/06* (2013.01); *A61K 35/32* (2013.01); *A61K 36/076* (2013.01); *A61K 36/21* (2013.01); *A61K 36/232* (2013.01); *A61K 36/258* (2013.01); *A61K 36/284* (2013.01); *A61K 36/39* (2013.01); *A61K 36/40* (2013.01); *A61K 36/428* (2013.01); *A61K 36/46* (2013.01); *A61K 36/54* (2013.01); *A61K 36/64* (2013.01); *A61K 36/708* (2013.01); *A61K 36/714* (2013.01); *A61K 36/756* (2013.01); *A61K 36/815* (2013.01); *A61K 36/8945* (2013.01); *A61P 13/12* (2018.01)

(58) Field of Classification Search
None
See application file for complete search history.

(56) References Cited

FOREIGN PATENT DOCUMENTS

CN  106728869 A  * 5/2017

* cited by examiner

*Primary Examiner* — Qiuwen Mi
(74) *Attorney, Agent, or Firm* — Bacon & Thomas, PLLC

(57) ABSTRACT

The present invention is directed to a therapeutic method of treatment of uremia associated with renal dysfunction long after transplant, comprising administering to a subject in need a therapeutically effective amount of a Chinese medicine composition. The Chinese medicine composition is the extract of the mixture including Fructus corni, radix Rehmanniae, rhizoma Dioscoreae, Radix Angelica sinensis, Cortex eucommiae, Semen cuscutae, Fructus lycii, Fructus Cinnamomum cassia, Radix aconiti lateralis preparata, Rhizoma Zingiberis, Poria, Phelloendron amurense Cortex, radix *Achyranthis Bidentatae*, and Atractylodes Lancea Rhizoma.

18 Claims, No Drawings

METHOD OF TREATMENT OF UREMIA ASSOCIATED WITH RENAL DYSFUNCTION LONG AFTER TRANSPLANT

BACKGROUND OF THE INVENTION

1. Field of the Invention

The present invention is directed to a method of treatment of uremia associated with renal dysfunction long after transplant; in particular, a method of increasing the renal excretion of uremic toxins.

2. Description of Related Art

The application of Chinese herbal medicine in treatment of diseases attracts significant attentions for a long time. In recent years, the Chinese medicine is also applied to treatment of some metabolic diseases.

Uremia is attributed to renal failure, rendering the kidney losing the native function, being incapable to excrete metabolite of protein, and having excessive blood urea. The compounds excreted by kidney include indole, phenol, guanidine, and other toxic compounds, and may contribute to toxicity and many other disease symptoms, such as headache, fatigue, peripheral neuropathy, acidosis, etc. Due to the presence of types of uremic toxins, the symptoms of uremia are not attributed to any single toxin and appear as syndrome. In present time, there is no effective medicine to completely cure uremia. The most effective treatment is dialysis which is used to ameliorate the symptoms. However, the use of dialysis is limited for the reason of incapability of cleaning small molecules. Furthermore, the symptoms of uremia can be improved by regulating diet. The patient can reduce the consumption of the foods which is more likely to produce toxins, or alter the gastrointestinal microflora to decrease the protein metabolism producing toxins. Additionally, the prior reports demonstrate the technique of adsorbent for oral administration that adsorb the toxins and can be excreted with feces.

For the reasons above, it is necessary to develop new drugs to improve uremia and lower down the blood uremic toxins and to provide alternative or adjuvant therapy which is more suitable for patients; in particular, to provide the therapy for the subject who is a patient of renal dysfunction and then transplant with a new kidney, wherein the new kidney degenerates to a atrophic and dysfunctional kidney and need dialysis, wherein the treatment transform the genitourinary tract cell and the gastrointestinal epithelial cell of the patient into uremic toxin-excreting cells.

SUMMARY OF THE INVENTION

The objective of the present invention is to provide a method of treatment of uremia associated with renal dysfunction long after transplant.

The method of treatment of uremia associated with renal dysfunction long after transplant comprises administering to a subject in need a therapeutically effective amount of a Chinese medicine composition; wherein the Chinese medicine composition is an extract of a first mixture comprising: Fructus corni, radix Rehmanniae, rhizoma Dioscoreae, Radix Angelica sinensis, Cortex eucommiae, Semen cuscutae, Fructus lycii, Fructus Cinnamomum cassia, Radix aconiti lateralis preparata, Rhizoma Zingiberis, Poria, Phelloendron amurense Cortex, radix *Achyranthis Bidentatae*, and Atractylodes Lancea Rhizoma.

In a preferred embodiment, the Chinese medicine composition is prepared by the following steps:
providing the first mixture;
mixing the first mixture and water to form a second mixture;
heating the second mixture to obtain a crude extract; and
filtering the crude extract and retaining the liquid, to obtain the Chinese medicine composition.

In a preferred embodiment, the first mixture comprises 2-6 parts by weight of Fructus corni, 2-6 parts by weight of radix Rehmanniae, 2-6 parts by weight of rhizoma Dioscoreae, 0.5-4 parts by weight of Radix Angelica sinensis, 2-6 parts by weight of Cortex eucommiae, 2-6 parts by weight of Semen cuscutae, 1-5 parts by weight of Fructus lycii, 3-7 parts by weight of Fructus Cinnamomum cassia, 1-5 parts by weight of Radix aconiti lateralis preparata, 1-5 parts by weight of Rhizoma Zingiberis, 1-5 parts by weight of Poria, 1-5 parts by weight of Phelloendron amurense Cortex, 3-7 parts by weight of radix *Achyranthis Bidentatae*, 1-5 parts by weight of Atractylodes Lancea Rhizoma.

In a preferred embodiment, the part by weight of the first mixture is 3.75 grain per part.

In a preferred embodiment, the method further comprises dialysis.

In a preferred embodiment, the first mixture further comprises: Radix Ginseng, Velvet antler, Radix Angelicae Sinensis, salt, gypsum powder, radix Rhubarb, Radix Trichosanthis, or the combination thereof.

In a preferred embodiment, the method is the treatment for lowering BUN and CR.

In a preferred embodiment, the Chinese medicine composition is administered via oral administration, enteral administration, or intravenous injection.

In a preferred embodiment, the Chinese medicine composition further comprises pharmaceutically acceptable carrier, stabilizer, diluent, dispersant, suspending agents, thickening agent, or excipient, or the combination thereof.

In a preferred embodiment, the method is for the subject who is a patient of renal dysfunction and then transplant with a new kidney, wherein the new kidney degenerates to a atrophic and dysfunctional kidney and need dialysis, wherein the treatment transform the genitourinary tract cell and the gastrointestinal epithelial cell of the patient into uremic toxin-excreting cells.

Another objective of the present invention is to provide a method of increasing the renal excretion of uremic toxin of a subject having renal dysfunction long after transplant.

DETAILED DESCRIPTION OF THE PREFERRED EMBODIMENT

The features of the present invention are set forth with particularity in the appended claims. A better understanding of the features and advantage thereof will be demonstrated by reference to the following detailed description that sets forth illustrative embodiments, in which the principles of the invention are employed.

Certain Pharmaceutical and Medical Terminology

Unless otherwise specified, the following terms used in the specification and claims have the definitions given below. It must be noted that, as used in the specification and the appended claims, the singular forms "a", "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology can be employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described. Unless otherwise indicated, all materials employed in the present invention are available in the ordinary markets.

The present invention provides a method of treatment which ameliorates the symptoms of uremia associated with renal dysfunction long after transplant, which includes but not limited to lower BUN and CR. In particular, the method is the treatment for the subject who is a patient of renal dysfunction and then transplant with a new kidney, wherein the new kidney degenerates to a atrophic and dysfunctional kidney and need dialysis, wherein the treatment transform the genitourinary tract cell and the gastrointestinal epithelial cell of the patient into uremic toxin-excreting cells.

The method of the present invention can be used to ameliorate the symptoms of uremia associated with renal dysfunction long after transplant, which includes but are not limited to fatigue, legs cramping, edema, headache, nausea and vomiting, trouble concentration, cardiovascular disease, itching, imbalance of blood minerals, amyloidosis, and acidosis.

The method of the present invention can be used to kidney-related diseases which include but are not limited to chronic kidney disease, kidney inflammation, glomerular nephritis, hyperuricemia, and nephrosis.

In particular, the present invention provides the therapy for the subject who is a patient of renal dysfunction and then transplant with a new kidney, wherein the new kidney degenerates to a atrophic and dysfunctional kidney and need dialysis, wherein the treatment transform the genitourinary tract cell and the gastrointestinal epithelial cell of the patient into uremic toxin-excreting cells.

The term "carrier" or "excipient" or the like, as used herein, refers to relatively nontoxic chemical compounds or agents that facilitate the incorporation of a compound into cells or tissues without interfering the effect of the treatment.

The term "diluent" or the like, as used herein, refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The aforementioned pharmaceutical vehicles can further comprise at least one selected from the group consisting of aromatics, buffering agents, binders, colorants, disintegrants, emulsifiers, extenders, flavor-improving agents, gellants, glidants, preservatives, skin-penetration enhancers, solubilizers, stabilizers, dispersing agents, suspending agents, sweeteners, tonicity agents, viscosity-increasing agents, or the combination thereof.

The term "pharmaceutically acceptable", as used herein, refers to the compounds, formulations, composition, and/or dose form, within the scope of reasonable medical judgment, suitable for contacting with the suffered subject, without undue detrimental effect, toxicity, irritation, allergic response, or any conditions or complications on the general health of the subject being treated, and commensurate with a reasonable benefit/risk ratio.

The term "effective amount" or "therapeutically effective amount", as used herein, refers to a sufficient amount of an agent or a compound being administered which will relieve one or more of the symptoms of the disease or condition being treated to some extent; the result thereof can be reduction and/or alleviation of the signs, symptoms, or causes of a disease, or any other desired alteration of a biological system. For example, an "effective amount" for therapeutic uses is the amount of the composition as disclosed herein required to provide a clinically significant decrease in disease symptoms. An appropriate "effective" amount in any individual case may be determined using techniques, such as a dose escalation study.

The term "enhance", "enhancing", or the like, as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

The term "treat," "treating", "treatment", or the like, as used herein, include alleviating, abating or ameliorating at least one symptom of a disease or condition, preventing disease progression, inhibiting the disease or condition, e.g., arresting the development of the disease or condition, relieving the disease or condition, causing regression of the disease or condition, relieving the condition caused by the disease or condition, or reducing the sign or symptoms of the disease or condition either prophylactically and/or therapeutically.

The present invention provides a method of treatment of uremia associated with renal dysfunction long after transplant, comprising administering to a subject in need a therapeutically effective amount of Chinese medicine composition; wherein the Chinese medicine composition is an extract of a first mixture comprising: Fructus corni, radix Rehmanniae, rhizoma Dioscoreae, Radix Angelica sinensis, Cortex eucommiae, Semen cuscutae, Fructus lycii, Fructus Cinnamomum cassia, Radix aconiti lateralis preparata, Rhizoma Zingiberis, Poria, Phelloendron amurense Cortex, radix *Achyranthis Bidentatae*, and Atractylodes Lancea Rhizoma.

In an embodiment, the Chinese medicine composition can be co-administered with another pharmaceutical composition according to the method of treatment of uremia. In a particular embodiment, the Chinese medicine composition and another pharmaceutical composition are administered simultaneously, concurrently or sequentially.

The dose forms of the Chinese medicine composition provided in the present invention includes but is not limit to solution, emulsion, suspension, powder, tablet, pill, lozenge, troche, chewing gum, capsule, or any dose form which is suitable for the Chinese medicine composition provided herein.

Preparation 1

The Chinese medicine composition used herein comprises the extract of the first mixture comprising the following materials: 2-6 parts by weight of Fructus corni (Cornus officinalis), 2-6 parts by weight of radix Rehmanniae (*Rehmannia glutinosa*), 2-6 parts by weight of rhizoma Dioscoreae (*Dioscorea opposita*), 0.5-4 parts by weight of Radix Angelica sinensis, 2-6 parts by weight of Cortex eucommiae (Eucommia ulmoides), 2-6 parts by weight of Semen cuscutae (Cuscuta chinensis), 1-5 parts by weight of Fructus lycii (Lycium barbarum), 3-7 parts by weight of Fructus Cinnamomum cassia, 1-5 parts by weight of Radix aconiti lateralis preparata (Acontium carmichaeli), 1-5 parts by weight of Rhizoma Zingiberis (Zingibor officinale), 1-5 parts by weight of Poria (*Wolfiporia cocos*), 1-5 parts by weight of Phelloendron amurense Cortex, 3-7 parts by weight of radix *Achyranthis Bidentatae*, and 1-5 parts by weight of Atractylodes Lancea Rhizoma; wherein it is a daily dose of the Chinese medicine composition when a part by weight of the first mixture is 3.75 g per part.

In specific, the Chinese medicine composition used herein comprises the extract of the first mixture comprising the following materials: 4 parts by weight of Fructus corni (Cornus officinalis), 4 parts by weight of radix Rehmanniae (*Rehmannia glutinosa*), 4 parts by weight of rhizoma Dioscoreae (*Dioscorea opposita*), 2 parts by weight of Radix Angelica sinensis, 4 parts by weight of Cortex eucommiae (Eucommia ulmoides), 4 parts by weight of Semen cuscutae (Cuscuta chinensis), 3 parts by weight of Fructus lycii (Lycium barbarum), 5 parts by weight of Fructus Cinnamomum cassia, 3 parts by weight of Radix aconiti lateralis preparata (Acontium carmichaeli), 3 parts by weight of Rhizoma Zingiberis (Zingibor officinale), 3 parts by weight of Poria (*Wolfiporia cocos*), 3 parts by weight of Phelloendron amurense Cortex, 5 parts by weight of radix *Achyranthis Bidentatae*, and 3 parts by weight of Atractylodes Lancea Rhizoma; wherein it is a daily dose of the Chinese medicine composition when a part by weight of the first mixture is 3.75 g per part.

In a further embodiment, the first mixture optionally comprise at least one selected from the group consisting of 0-3 g Radix Ginseng, 0-3 g Velvet antler, 0-3 g, Radix Angelicae Sinensis, 0-3 g salt, 0-5 g gypsum ($CaSO_4.2H_2O$) powder, 0-3 g radix Rhubarb (Rheum palmatum, R. tanguticum, or R. officinale), 2-4 g, Radix Trichosanthis (Trichosanthes kirilowii), or the combination thereof.

The components of the first mixture are heated and extracted in a solvent; wherein the component of the first mixture can be optionally grinded before extraction to achieve the best extraction outcome, except that gypsum powder should be extracted in powder. The preferred solvent of the extraction is water, ethanol, DMSO (Dimethyl sulfoxide), or the combination thereof.

In a preferred embodiment of the present invention, the components of the daily dose of the Chinese herbal medicine are dissolved in 1,800-2,200 ml water to obtain a second mixture; the second mixture is heated at 100-120° C. for 1 hour and then the residue is filtered out to obtain the liquid extract. Preferably, the liquid extract is equally divided into 3 doses for ter in die administration. Preferably, the second mixture is heated at 100-120° C. for 1 hour and then the volume of the liquid extract after filtration is 400-500 ml.

Furthermore, the preparation method of the Chinese herbal medicine can include the step of concentration as follows: after the residue of the extract is filtered out, the liquid extract is condensed by vacuum or low pressure concentration under the condition of 50-60° C. and 20-40 torr, in order to obtain the condensate; preferably, the volume of the condensate is ¹/₁₀-¹/₂₀ volume of the liquid extract.

Furthermore, the corn starch used as an excipient is added to the condensate to obtain Chinese herbal paste; wherein the quantity of the corn starch depends on the stability of condensate; wherein the paste is optionally subject to granulation by spray-drying method.

Preparation 2

The preparation method of preparation 2 is similar to preparation 1, except that the first mixture further comprises 0.7 g Radix Ginseng, 0.3 g Velvet antler, and 1.0 g Radix Angelicae Sinensis, to obtain the composition of preparation 2 (daily dose).

Preparation 3

The preparation method of preparation 3 is similar to preparation 1, except that the first mixture further comprises 1.0 g Radix Ginseng, 1.0 g Velvet antler, 0.3 g radix Rhubarb, and 0.5 g salt, to obtain the composition of preparation 3.

Preparation 4

The preparation method of preparation 4 is similar to preparation 1, except that the first mixture further comprises 1.0 g Radix Ginseng, 2.0 g Velvet antler, 1.0 g radix Rhubarb, 1.5 g salt, and 1.0 g gypsum powder, to obtain the composition of preparation 4.

Preparation 5

The preparation method of preparation 5 is similar to preparation 1, except that the first mixture further comprises 3.0 g Radix Trichosanthis, and 3.0 g gypsum powder, to obtain the composition of preparation 5.

Example 1

The patient of uremia associate with renal dysfunction long after transplant in example 1 had the blood test result that BUN (blood urea nitrogen) was 34.2; CR (creatine) was 7.55; the patient has a transplanted kidney which is chronically atrophic, and has to employ dialysis to control the uremia.

The treatment of the patient of uremia comprised administering the Chinese medicine composition according to preparation 2 continuously for approximately 1.5 month.

After the patient continuously administered the Chinese medicine composition according to preparation 2 for 1.5 month, BUN was lowered to 32.0 and CR was lower to 7.4. Subsequently, the patient was administered the Chinese medicine composition according to preparation 3 continuously for approximately 3.5 month.

After the patient continuously administered the Chinese medicine composition according to preparation 3 for 3.5 month, BUN was lowered to 29.2 and CR was lower to 6.16. Subsequently, the patient was administered the Chinese medicine composition according to preparation 4 continuously for approximately 1.5 month.

After the patient continuously administered the Chinese medicine composition according to preparation 4 for 1.5 month, BUN was lowered to 27.2 and CR was 6.66, which is not lower but did not recover to high level, either. Subsequently, the patient was administered the Chinese medicine composition according to preparation 1 continuously for approximately 7 month.

After the patient continuously administered the Chinese medicine composition according to preparation 1 for 7 month, BUN was lowered to 23.4 and CR was maintained at 6.8.

In sum of the above, the Chinese medicine composition can effectively lower down or maintain the excessive level of BUN and CR and can be used to treat the uremia associated with renal dysfunction long after transplant.

While the preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents are covered thereby.

What is claimed is:

1. A method of treatment of uremia associated with renal dysfunction long after transplant, comprising administering to a subject in need a therapeutically effective amount of a Chinese medicine composition;
   wherein the Chinese medicine composition is an extract of a first mixture comprising: Fructus corn, radix Rehmanniae, rhizoma Dioscoreae, Radix Angelica sinensis, Cortex eucommiae, Semen cuscutae, Fructus lycii, Fructus Cinnamomum cassia, Radix aconiti lateralis preparata, Rhizoma Zingiberis, Poria, Phelloendron amurense Cortex, radix *Achyranthis Bidentatae*, and Atractylodes Lancea Rhizoma.

2. The method as claimed in claim 1, wherein the Chinese medicine composition is prepared by the following steps:
   providing the first mixture;
   mixing the first mixture and water to form a second mixture;
   heating the second mixture to obtain a crude extract; and
   filtering the crude extract and retaining the liquid, to obtain the Chinese medicine composition.

3. The method as claimed in claim 1, wherein the first mixture comprises 2-6 parts by weight of Fructus corni, 2-6 parts by weight of radix Rehmanniae, 2-6 parts by weight of rhizoma Dioscoreae, 0.5-4 parts by weight of Radix Angelica sinensis, 2-6 parts by weight of Cortex eucommiae, 2-6 parts by weight of Semen cuscutae, 1-5 parts by weight of Fructus lycii, 3-7 parts by weight of Fructus Cinnamomum cassia, 1-5 parts by weight of Radix aconiti lateralis preparata, 1-5 parts by weight of Rhizoma Zingiberis, 1-5 parts by weight of Poria, 1-5 parts by weight of Phelloendron amurense Cortex, 3-7 parts by weight of radix *Achyranthis Bidentatae*, 1-5 parts by weight of Atractylodes Lancea Rhizoma.

4. The method as claimed in claim 3, wherein the part by weight of the first mixture is 3.75 grain per part.

5. The method as claimed in claim 1, wherein the method further comprises dialysis.

6. The method as claimed in claim 1, wherein the first mixture further comprises: Radix Ginseng, Velvet antler, Radix Angelicae Sinensis, salt, gypsum powder, radix Rhubarb, Radix Trichosanthis, or the combination thereof.

7. The method as claimed in claim 1, wherein the method is the treatment for lowering BUN and CR.

8. The method as claimed in claim 1, wherein the Chinese medicine composition is administered via oral administration, enteral administration, or intravenous injection.

9. The method as claimed in claim 1, wherein the Chinese medicine composition further comprises pharmaceutically acceptable carrier, stabilizer, diluent, dispersant, suspending agents, thickening agent, or excipient, or the combination thereof.

10. The method as claimed in claim 1, wherein the method is for the subject who is a patient of renal dysfunction and then transplant with a new kidney, wherein the new kidney degenerates to a atrophic and dysfunctional kidney and need dialysis, wherein the treatment transform the genitourinary tract cell and the gastrointestinal epithelial cell of the patient into uremic toxin-excreting cells.

11. A method of increasing the renal excretion of uremic toxin of a subject having renal dysfunction long after transplant, comprising administering to a subject in need a therapeutically effective amount of a Chinese medicine composition;
    wherein the Chinese medicine composition is an extract of a first mixture comprising: Fructus corn, radix Rehmanniae, rhizoma Dioscoreae, Radix Angelica sinensis, Cortex eucommiae, Semen cuscutae, Fructus lycii, Fructus Cinnamomum cassia, Radix aconiti lateralis preparata, Rhizoma Zingiberis, Poria, Phelloendron amurense Cortex, radix *Achyranthis Bidentatae*, and Atractylodes Lancea Rhizoma.

12. The method as claimed in claim 11, wherein the preparation method of the Chinese medicine composition is prepared by following steps:
    providing the first mixture;
    mixing the first mixture and water to form a second mixture;
    heating the second mixture to obtain a crude extract; and
    filtering the crude extract and retaining the liquid, to obtain the Chinese medicine composition.

13. The method as claimed in claim 11, wherein the first mixture comprises 2-6 parts by weight of Fructus corni, 2-6 parts by weight of radix Rehmanniae, 2-6 parts by weight of rhizoma Dioscoreae, 0.5-4 parts by weight of Radix Angelica sinensis, 2-6 parts by weight of Cortex eucommiae, 2-6 parts by weight of Semen cuscutae, 1-5 parts by weight of Fructus lycii, 3-7 parts by weight of Fructus Cinnamomum cassia, 1-5 parts by weight of Radix aconiti lateralis preparata, 1-5 parts by weight of Rhizoma Zingiberis, 1-5 parts by weight of Poria, 1-5 parts by weight of Phelloendron amurense Cortex, 3-7 parts by weight of radix *Achyranthis Bidentatae*, 1-5 parts by weight of Atractylodes Lancea Rhizoma.

14. The method as claimed in claim 13, wherein the part by weight of the first mixture is 3.75 grain per part.

15. The method as claimed in claim 11, wherein the method further comprise dialysis.

16. The method as claimed in claim 11, wherein the first mixture further comprises: Radix Ginseng, Velvet antler, Radix Angelicae Sinensis, salt, gypsum powder, radix Rhubarb, Radix Trichosanthis, or the combination thereof.

17. The method as claimed in claim 11, wherein the Chinese medicine composition is administered via oral administration, enteral administration, or intravenous injection.

18. The method as claimed in claim 10, wherein the Chinese medicine composition further comprises pharmaceutically acceptable carrier, stabilizer, diluent, dispersant, suspending agents, thickening agent, or excipient, or the combination thereof.

* * * * *